US011275020B2

(12) United States Patent
Hatamian

(10) Patent No.: US 11,275,020 B2
(45) Date of Patent: Mar. 15, 2022

(54) LATERAL FLOW ASSAY HOUSING AND METHOD OF CORRECTING COLOR, INTENSITY, FOCUS, AND PERSPECTIVE OF AN IMAGE OF THE TEST RESULTS

(71) Applicant: Mehdi Hatamian, Mission Viejo, CA (US)

(72) Inventor: Mehdi Hatamian, Mission Viejo, CA (US)

( * ) Notice: Subject to any disclaimer, the term of this patent is extended or adjusted under 35 U.S.C. 154(b) by 0 days.

(21) Appl. No.: 17/343,627

(22) Filed: Jun. 9, 2021

(65) Prior Publication Data

US 2021/0389233 A1    Dec. 16, 2021

Related U.S. Application Data

(60) Provisional application No. 63/038,073, filed on Jun. 11, 2020.

(51) Int. Cl.
| | | |
|---|---|---|
| *G01N 21/05* | (2006.01) | |
| *G01N 33/543* | (2006.01) | |
| *G01N 27/08* | (2006.01) | |
| *G01N 21/77* | (2006.01) | |

(52) U.S. Cl.
CPC .............. *G01N 21/05* (2013.01); *G01N 27/08* (2013.01); *G01N 33/543* (2013.01); *G01N 2021/7759* (2013.01); *G01N 2021/7763* (2013.01)

(58) Field of Classification Search
CPC .... G01N 21/05; G01N 27/08; G01N 27/3275; G01N 33/543; G01N 33/53; G01N 33/558; G01N 33/743; G01N 2021/7759; G01N 2021/7763; B01L 3/502; B01L 2200/026
See application file for complete search history.

(56) References Cited

U.S. PATENT DOCUMENTS

| | | | |
|---|---|---|---|
| 7,888,043 B2 * | 2/2011 | Castro | G01N 33/571 435/7.1 |
| 2014/0154789 A1 * | 6/2014 | Polwart | G01N 33/5302 435/287.2 |
| 2016/0274104 A1 * | 9/2016 | Aminoff | G01N 33/743 |
| 2017/0234866 A1 * | 8/2017 | Hamad-Schifferli | G01N 33/54306 506/9 |
| 2018/0045723 A1 * | 2/2018 | Makinen | G01N 33/54386 |
| 2019/0376966 A1 * | 12/2019 | Pulitzer | G01N 21/77 |
| 2020/0078781 A1 * | 3/2020 | Beckley | B01L 3/50 |
| 2020/0346209 A1 * | 11/2020 | Riester | B01L 3/5023 |

\* cited by examiner

*Primary Examiner* — Sang H Nguyen
(74) *Attorney, Agent, or Firm* — Makoui Law, PC; Ali Makoui

(57) ABSTRACT

A lateral flow assay device includes several markers, a color bar, and/or a grayscale on the housing of the lateral flow assay device. The markers are used to assist in focusing a mobile device's camera on the control line of the lateral flow assay device. The markers may be used to adjust the perspective of an image taken from the control line and the test line of the lateral flow assay device. The markers may be used to locate the images of the control line, the test line, the color bar, and/or the grayscale on the image. The image of the color bar and the grayscale may be used to adjust the colors and intensity of the image. The images of the test line and the control line may then be used to determine the test results of the lateral flow assay device.

20 Claims, 9 Drawing Sheets

LATERAL FLOW ASSAY HOUSING AND METHOD OF CORRECTING COLOR, INTENSITY, FOCUS, AND PERSPECTIVE OF AN IMAGE OF THE TEST RESULTS

CLAIM OF BENEFIT TO PRIOR APPLICATIONS

This application claims the benefit of U.S. Provisional Patent Application Ser. No. 63/038,073, filed on Jun. 11, 2020. The contents of U.S. Provisional Patent Application 63/038,073 are hereby incorporated by reference.

BACKGROUND

A Lateral flow assay (LFA), also referred to as lateral flow immunochromatographic assay or lateral flow dipstick immunoassay, is a device that is used to detect the presence (or absence) of a target analyte in a sample fluid without the need for specialized equipment. The lateral flow assays are widely used for medical diagnostics for point of care testing, home testing, or laboratory use.

A lateral flow assay typically includes a series of capillary pads for transporting fluid. A sandwich assay format may be used for detecting analytes that have at least two binding sites to bind to antibodies. A sample pad is used to receive a quantity of fluid (referred to as the sample fluid) and transport the sample fluid to an adjacent conjugate pad. The conjugate pad contains a solubilized antibody labeled with a detector such as colloidal gold nanoparticles. The antibody is specific to a certain analyte which is the target of interest in the sample fluid. Some lateral flow assays may not have a sample pad. In these assays, the sample may be directly applied to the conjugate pad. As the sample fluid flows through the conjugate pad, the analyte (if any) in the sample fluid binds with the labeled antibody on the conjugate pad and forms an immunocomplex.

The immunocomplex then flows from the conjugate pad into an adjacent membrane (or membrane pad). The membrane has one or more test lines. Each test line may contain an immobilized unlabeled antibody. As the immunocomplex moves over a test line, the immunocomplex binds with the immobilized antibody on the test line, resulting in a colored test line. When the sample fluid does not include the target analyte, no immunocomplex is formed on the conjugate pad and no immunocomplex binds with the immobilized antibody on the test line. As a result, the test line does not change color.

A lateral flow assay may also include a control line on the membrane. In a sandwich assay format, the control line may contain an immobilized antibody that binds to the free antibodies labeled with the detector resulting in a colored control line, which confirms that the test has operated correctly regardless of whether or not the target analyte has been present in the sample.

A competitive assay format may be used for detecting analytes that cannot simultaneously bind to two antibodies. The sample pad and the conjugate pad in a competitive assay format are similar to the sample pad and the conjugate pad in the sandwich assay format. In the competitive assay format, the test line contains immobilized analyte molecules.

If the sample liquid does not contain the analyte, the labeled antibody flows from the conjugate pad into the test line and binds to the analyte at the test line, resulting in a colored test line that indicates the lack of the target analyte in the sample liquid. If, on the other hand, the target analyte is present in the sample liquid, the analyte binds to the labeled antibodies on the conjugate pad and prevents the labeled antibody to bind to the analyte at the test line, resulting in the lack of color on the test line. In a competitive assay format, the control line may contain an immobilized analyte that binds to the free antibodies labeled with the detector resulting in a colored control line, which confirms that the test has operated correctly regardless of whether or not the target analyte has been present in the sample.

BRIEF DESCRIPTION OF THE DRAWINGS

The various embodiments of the present lateral flow assay housing and method of correcting color, intensity, focus, and perspective of an image of the test results now will be discussed in detail with an emphasis on highlighting the advantageous features. These embodiments depict the novel and non-obvious lateral flow assay housing and method of correcting color, intensity, focus, and perspective of an image of the test results shown in the accompanying drawings, which are for illustrative purposes only. These drawings include the following figures, in which like numerals indicate like parts.

DETAILED DESCRIPTION

Figure 1A:
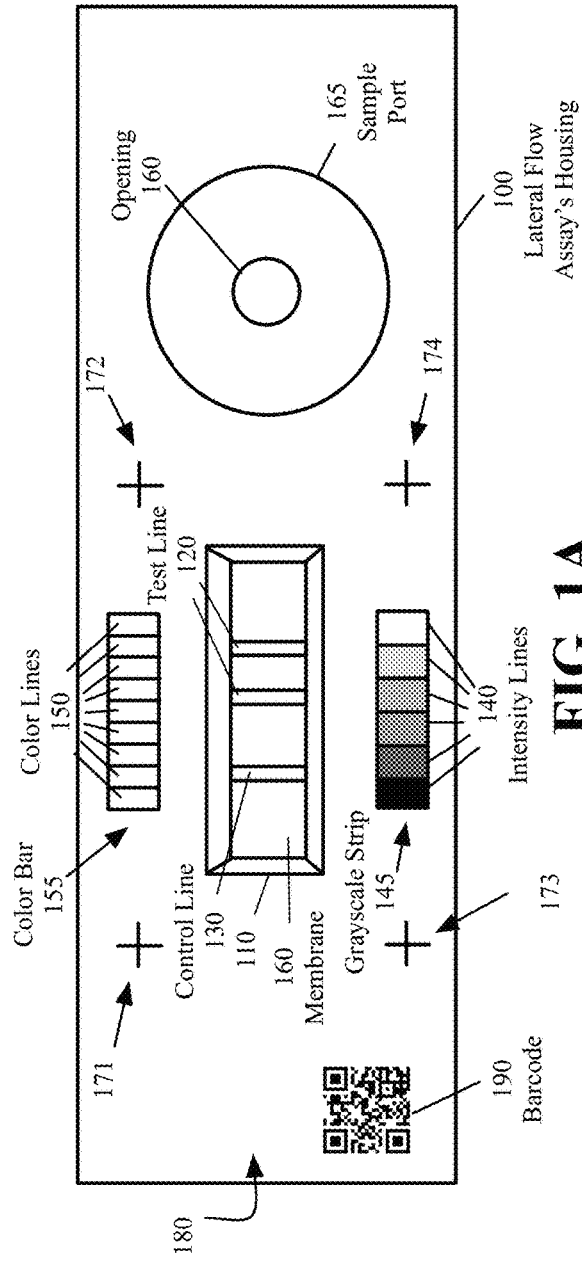
FIG. 1A is a top plan view of one example embodiment of a lateral flow assay device with a color bar, a grayscale strip and a two-dimensional bar code, according to various aspects of the present disclosure.

One aspect of the present embodiments includes the realization that taking a picture of a lateral flow assay device's test line may result in an image that may depend on the lighting condition, distance of the camera lens to the test line, the angle of the camera with respect to the plane of the membrane, the quality and the type of the camera lens, etc. The appearance of the test line and the control line may, therefore, be sensitive to the variations in the environment and equipment. These variations may cause inconsistency in the interpretation of the test results by a computer or other lab equipment.

Some of the present embodiments solve the aforementioned problems by including several markers, a color bar, and/or a grayscale on the housing of a lateral flow assay device. The markers may be used to assist in focusing a mobile device's camera on the control line of the lateral flow assay device. The markers may also be used to adjust the perspective of an image taken from the control line and the test line(s) of the lateral flow assay device.

The markers may also be used to locate the images of the control line, the test line(s), the color bar, and/or the grayscale on the image. The image of the color bar and the grayscale may be used to adjust the colors and intensity of the image. The images of the test line(s) and the control line may then be used to determine the test results of the lateral flow assay device.

In addition to, or in lieu of the markers, some embodiments may process one or more images of the lateral flow assay device and find the location of the color bar, the grayscale strip, and/or the control line by finding the patterns that correspond to the color bar, the grayscale strip, and/or the control line, respectively. The images may be processed, for example, and without limitations, by searching the images for groups of pixels with color values that closely match the known color values of pixels of the color bar's color lines, by searching the images for groups of pixels with intensity values that closely match the known intensity values of pixels of the grayscale strip's intensity lines, and/or by searching the images for groups of pixels that both closely match the known color values of control line after the control line is turned on and also form a narrow line with contrast to its background (normally close to a white background). The relative distances of the color bar, the grayscale strip, and/or the control may then be used to find the location of test line(s).

The remaining detailed description describes the present embodiments with reference to the drawings. In the drawings, reference numbers label elements of the present embodiments. These reference numbers are reproduced below in connection with the discussion of the corresponding drawing features.

Figure 1B:
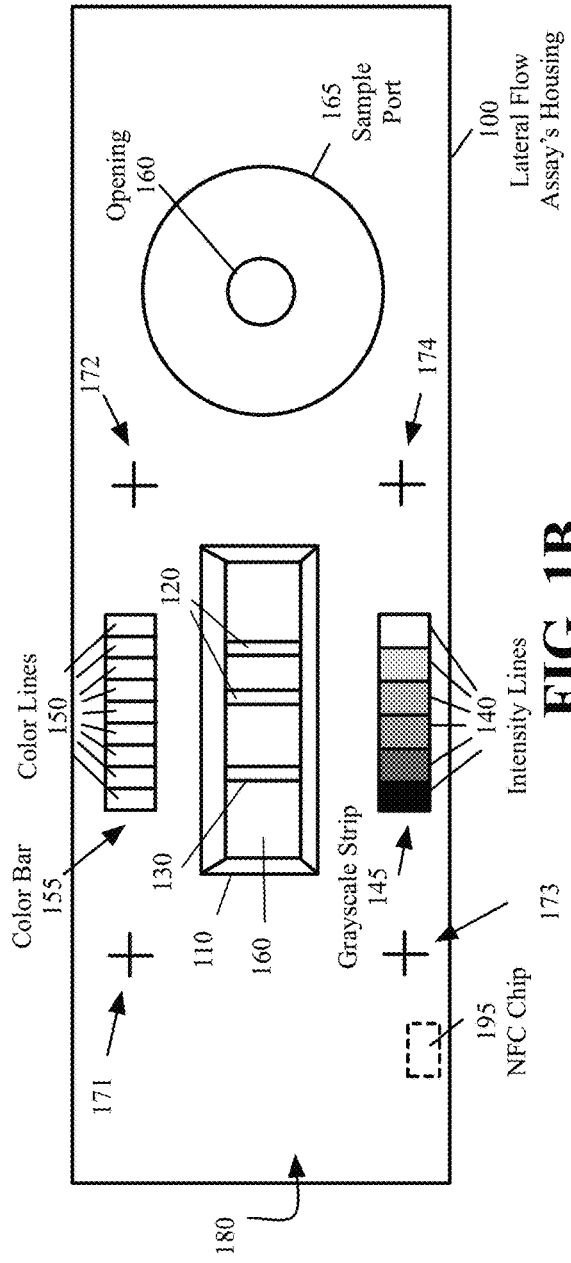
FIG. 1B is a top plan view of one example embodiment of a lateral flow assay device with a color bar, a grayscale strip and a near-field communication chip, according to various aspects of the present disclosure.

FIG. 1A is a top plan view of one example embodiment of a lateral flow assay device's housing 100 with a color bar, a grayscale strip, and a two-dimensional bar code, according to various aspects of the present disclosure. FIG. 1B is a top plan view of one example embodiment of a lateral flow assay device with a color bar, a grayscale strip, and a near-field communication chip, according to various aspects of the present disclosure. In this specification, the terms lateral flow assay device and lateral flow assay are interchangeably used to refer to a device that performs lateral flow tests.

With reference to FIGS. 1A-1B, the lateral flow assay device's housing 100 may be part of a replaceable cartridge that may be intended for single use. The lateral flow assay device's housing 100 may include a sample port 165 with an opening 160 for applying a sample, through the sample hole, to the sample pad. The lateral flow assay device's housing 100 may include an opening 110, referred to herein as the test results viewing window, for viewing the lateral flow assay device's test results. The lateral flow assay device may include one or more test lines 120 and a control line 130.

In a lateral flow assay test, the control line may contain an immobilized antibody (in a sandwich assay format) or an immobilized analyte (in a competitive assay format) that binds to the free antibodies labeled with the detector resulting in a colored control line. The control line, therefore, confirms that the test has operated correctly regardless of whether or not the target analyte has been present in the sample. As described below with reference to FIG. 4, some embodiments may provide a mobile application that may be used to take one or more images of the test line(s) 120 and the control line 130 of the lateral flow assay device, for example, and without limitations, after a certain binding time period specified by the test manufacturer of the test (e.g., on the order of 10 to 20 minutes) is passed and the control line has also changed color confirming that the test has operated correctly.

In some of the present embodiments, the lateral flow assay device's enclosure 100 may include a barcode 190 (FIG. 1A) and/or a near field communication (NFC) chip 195 (FIG. 1B), several markers 171-174, a color bar 155, and/or a grayscale strip 145 in order to identify the type of the lateral flow assay device's enclosure and to correct the images (e.g., perspective correction and/or color and intensity correction) taken by the camera of a mobile device from the lateral flow assay's test viewing window 100. Although four markers 171-174 are shown in several examples described herein, other embodiments may include a different number of markers.

The bar code 190, in some embodiments may be, for example, and without limitations, a one-dimensional (1D) or a two-dimensional (2D) barcode. The bar code 190 and/or the NFC chip 195 may identify the type (e.g., and without limitations, the model) of the lateral flow assay device, the type of test(s) to be performed by the lateral flow assay device, other parameters and information related to the test, etc. The bar code 190 and/or the NFC chip 195 may also include a unique serial number used for authentication.

Once the model of the lateral flow assay device is known, the distances between different items on the housing, such as the markers 171-174, the color bar 155, the color lines 150 on the color bar 155, the grayscale 145, the intensity lines 140 on the grayscale 145, the test results viewing window 110, etc., may be determined.

The markers 171-174, in some embodiments, may be used as reference points for framing the test viewing window 110 inside a particular region on the display of the mobile device. The image of the markers may then be used to locate the image of the control line 130 on the display of the mobile device and focus the camera of the mobile device on the control line 130. For example, and without limitations, the image of the markers and the known relative distance of the at least three markers to any particular point may be used to triangulate and find the particular point on the image.

The term relative distance is referred, herein, to normalized distances between different points. In some embodiments, the relative distance between any two points of interest on the lateral flow assay device may be determined by dividing the distance between the two points by a distance between two specific points on the lateral flow assay device.

For example, and without limitations, the distance between the two markers 171 and 173 may be used as a unit of measurement and the distance between any other pair of points may be normalized by dividing the distance by this unit of measurement. For instance, in one lateral flow assay model, the relative distance between the markers 172 and 173 may be 1.000, the relative distance between the marker 171 and the lower corner of the color bar 155 may be 0.350, the relative distance between the markers 171 and 172 may be 1.442, etc. Any distance between any two known points on the lateral flow assay model (e.g., the distance between two specific corners of the color bar, the length of the control line, etc.) may be used as the unit of measurement to determine the relative distance between different pairs of points on the lateral flow assay device. The location and the relative distances of the markers 171-174, the color bar 155, the grayscale strip 145, the control line 130, the test line(s) 120, etc., may be the same or different in different models of the lateral flow assay devices of the present embodiments.

In some embodiments, the relative distances between one or more of the makers, one or more points on the color bar, one or more points on the control line, one or more points on the test line(s), and/or one or more points on the grayscale strip for each model of the lateral flow assay device may be stored in one or more tables. In some embodiments, in addition to, or in lieu of the relative distances, the actual distances (e.g., in millimeters, inches, etc.) between one or more of the makers, one or more points on the color bar, one or more points on the control line, one or more points on the test line(s), and/or one or more points on the grayscale strip for each model of the lateral flow assay device may be stored in one or more tables. In some of these embodiments, the stored actual distances may be used to calculate the relative distance. In some of these embodiments, the actual distances may be used to determine the location of different objects in the images taken from the lateral flow assay device.

With reference to FIGS. 1A-1B, the control line 130 and the test line(s) 120 may be on the same plane inside the test results viewing window 110. Since the control line 130 and the test line(s) 120 are on the membrane 160 of the lateral flow assay device, the control line 130 and the test line(s) 120 are on a different plane than the surface 180 of the housing 100. Focusing on the control line may, therefore, produce a sharper image of the control line 130 and the test line(s) 120 than focusing on the surface 180 of the housing 100.

The image of the markers 171-174 may also be used to correct the perspective of an image taken to determine the test results of the lateral flow assay device. The color bar 155 may include several color lines 150 that may be used to correct the color of the images taken from the test results. The grayscale strip 145 may include several intensity lines 140 that may be used to correct the intensity of the images takes from the test results. The color bar 155 and grayscale strip 145 may also both be used together to collectively correct the color and intensity of the images.

The markers 171-174, the color bar 155, and/or the grayscale strip 145, in some embodiments, may be marked on the housing 100 at the time of manufacturing of the housing 100. In other embodiments, the markers 171-174, the color bar 155, and/or the grayscale strip 145 may be printed on one or more labels that may be affixed on the housing 100.

Figure 2:
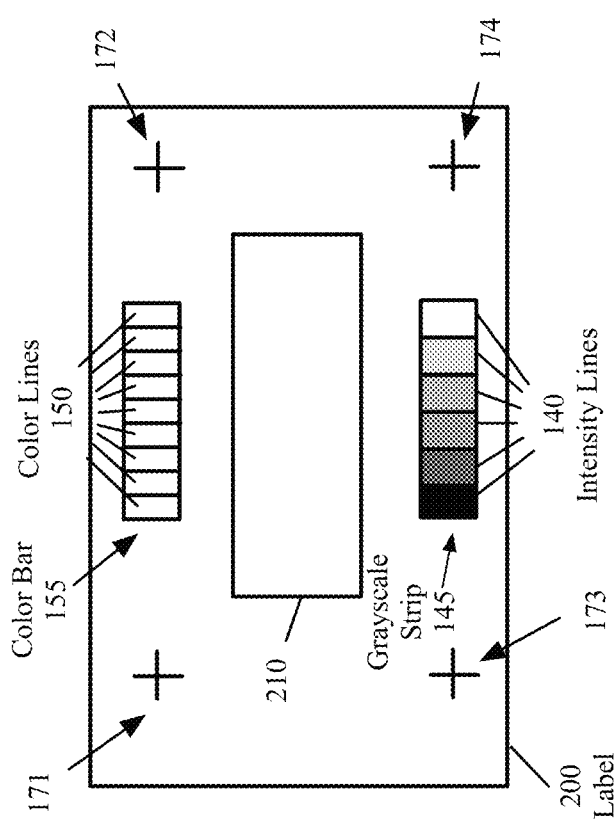
FIG. 2 is a top plan view of one example embodiment of a label with several markers, a color bar, and grayscale strip that may be placed on a lateral flow assay device's housing according to various aspects of the present disclosure.

FIG. 2 is a top plan view of one example embodiment of a label with several markers, a color bar, and grayscale strip that may be placed on a lateral flow assay device's housing according to various aspects of the present disclosure. With reference to FIG. 2, the label 200 may include several markers 171-174, a color bar 155, and/or a grayscale strip 145.

The label 200 may be placed on the top portion of the lateral flow assay device's housing 100 of FIGS. 1A-1B (e.g., on the side where the test viewing window 110 is located). The label 200 may cover all or a portion of top of the housing 100. In the example of FIG. 2, the label 200 is configured to cover a portion of the top of the housing 100. The label 200 may include on opening 210 that may fit over the test viewing window 110 of the housing 100.

The barcode 190 (FIG. 1A) or the NFC chip (FIG. 1B) may include information regarding the type of the lateral flow assay device's housing 100. The type of the housing 100 may, for example, determine the dimensions of the housing 100, the size of the test viewing window 110, etc., in order to allow the selection of the proper label 200 for placing on the lateral flow assay device's housing 100.

Figure 3:
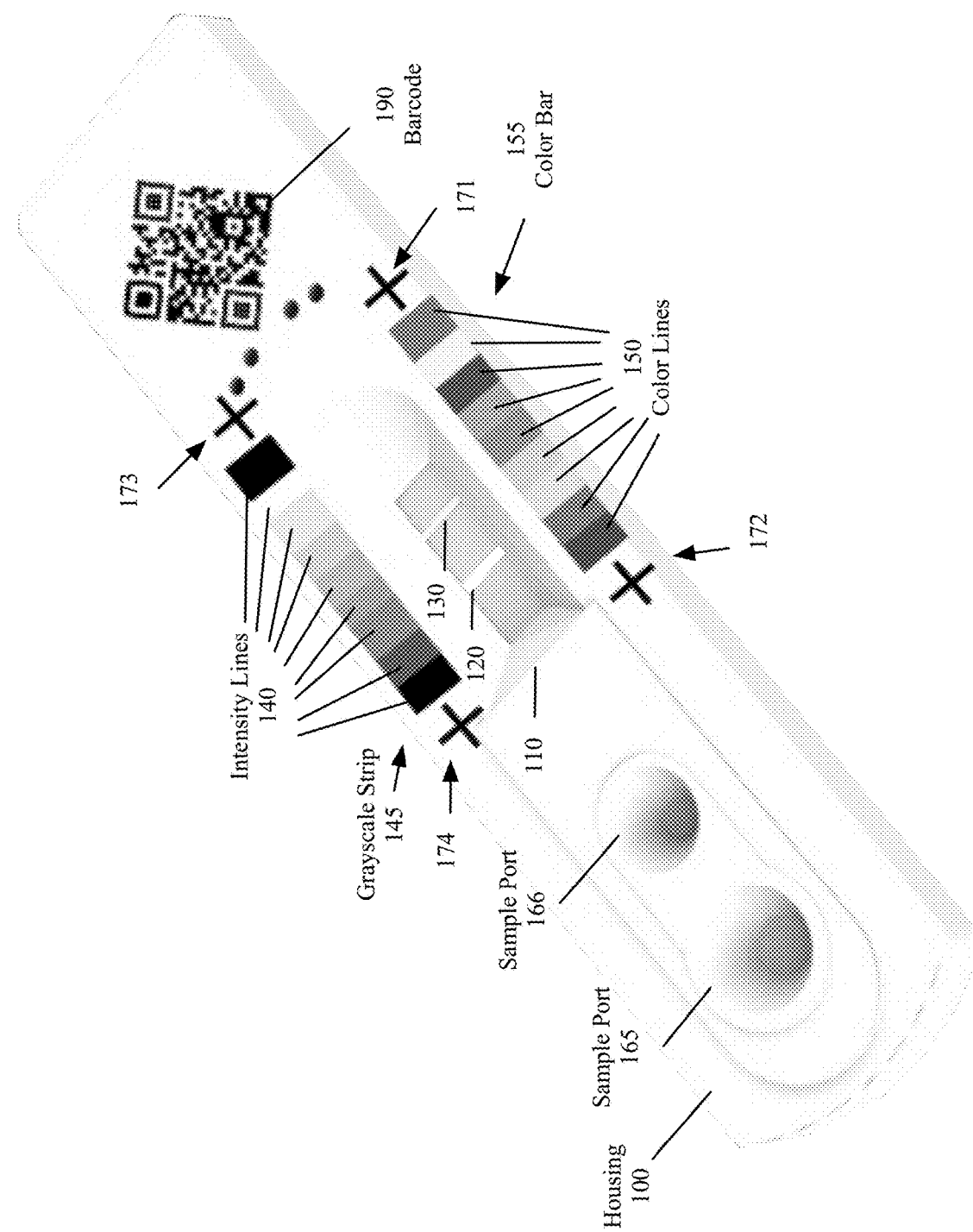
FIG. 3 is a top perspective view of a lateral flow assay device, according to various aspects of the present disclosure.

FIG. 3 is a top perspective view of a lateral flow assay device, according to various aspects of the present disclosure. With reference to FIG. 3, the lateral flow assay device's housing 100 may include the markers 171-174, the color bar 155, the color lines 150, the grayscale strip 145, and the intensity lines 140.

In the example of FIG. 3, the lateral flow assay device may have two sample ports 165 and 166 (e.g., and without limitations, one for applying a sample and the other for applying a buffer solution), one test line 120, the control line 130, the test results viewing window 110, and the bar code 190.

Figure 4:
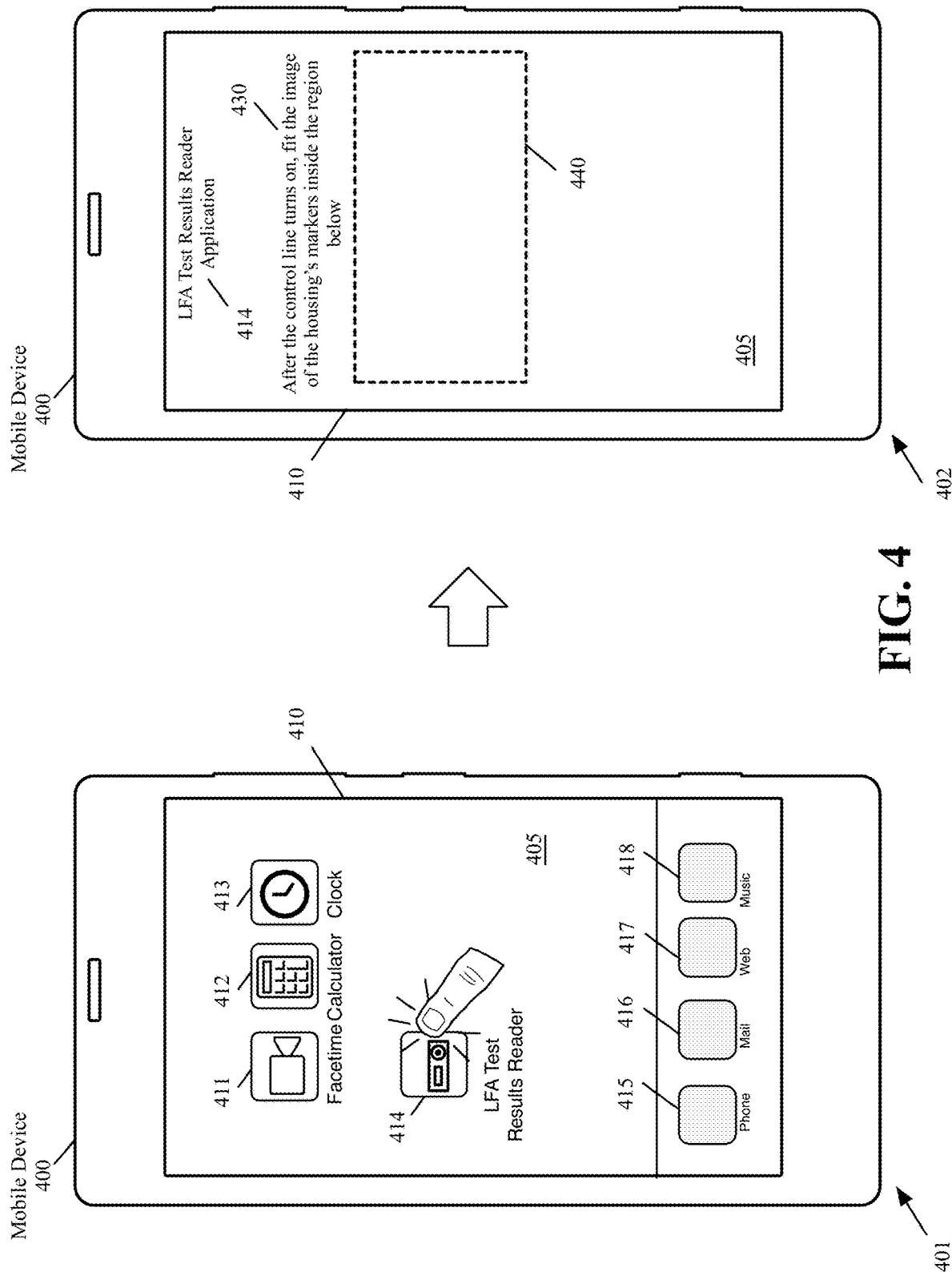
FIG. 4 is a schematic front view of a mobile device that includes an application program for taking an image of a lateral flow assay's test results, according to various aspects of the present disclosure.

FIG. 4 is a schematic front view of a mobile device 400 that includes an application program for taking an image of a lateral flow assay device's test results, according to various aspects of the present disclosure. The figure, as shown, includes two stages 401-402.

With reference to FIG. 4, stage 401 shows a user interface (UI) 405 displayed on a display (e.g., a touchscreen) 410 of the mobile device 400. The mobile device may be, for example, and without limitations, a smartphone, a tablet, a laptop computer, a smart watch, etc., that may include a camera. The UI 405 may include several selectable UI items (e.g., icons) of several applications 411-418. As shown, the LFA test results reader application 414 is selected in stage 401.

In response to the selection of the test results reader application 414, the UI 405, in stage 402, may activate the test results reader application 414. The test results reader application 414 may be a program that is installed on the mobile device 400 to read the test results of lateral flow assay devices.

The LFA test results reader application 414, in stage 402, may turn on the camera of the mobile device 400. The UI 405, in stage 402, may display a region 440 on the display 410 of the mobile device 400. The UI 405 may display a message 430 instructing the image of the lateral flow assay housing's markers 171-174 (FIGS. 1A-1B) to be fitted inside the region 440 after the control line turns on. Alternatively, the UI 405, in some embodiments, may display four markers on the display 410 of the mobile device 400 and may instruct the user to lineup the images of the markers 171-174 on the displayed markers.

The test results of the lateral flow assay device may be ready to be read when a certain binding time period specified by the test manufacturer is passed after the application of the sample, and the control line 130 also turns on. The binding time period depends on the test being performed and is usually on the order of 10 to 20 minutes, which may be specified.

Figure 5:
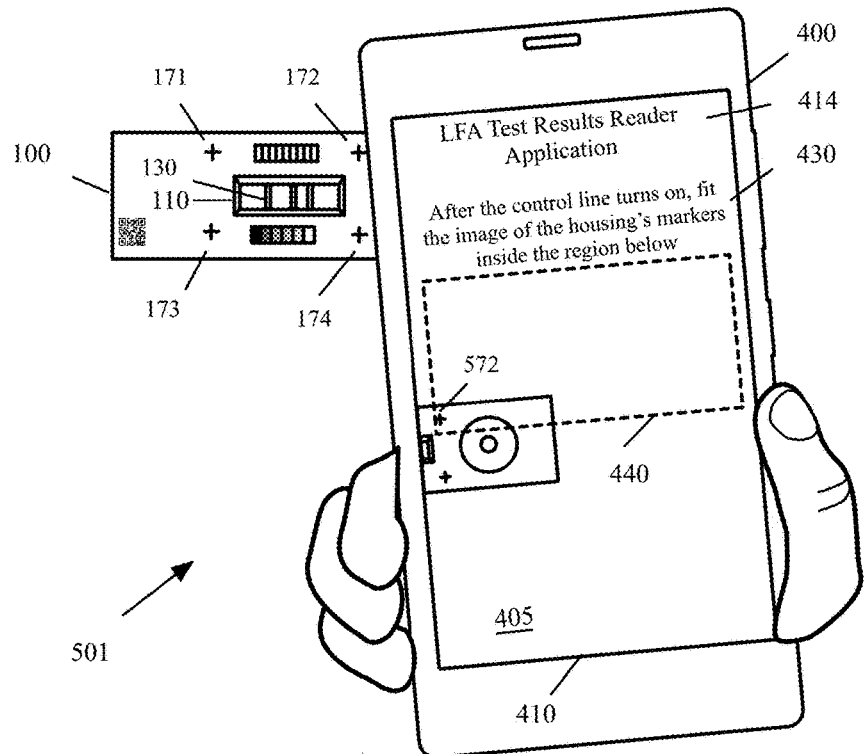
FIG. 5 is a functional diagram illustrating an example use of an application program for fitting the image of the markers on the housing of a lateral flow assay device in a region displayed on a mobile device in order to focus the mobile device's camera prior to taking an image of the test results of the lateral flow assay device, according to various aspects of the present disclosure.
Figure 5:
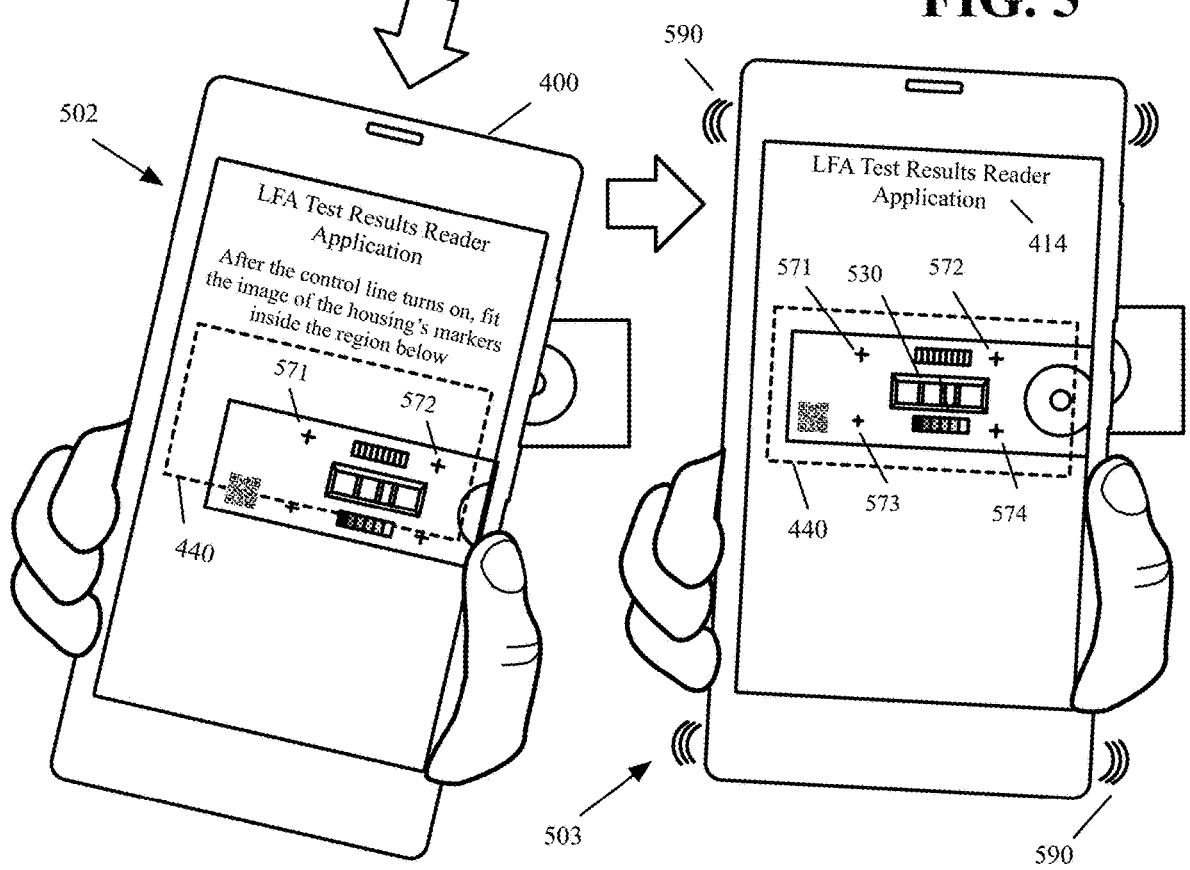

FIG. 5 is a functional diagram illustrating an example use of an application program for fitting the image of the markers on the housing of a lateral flow assay device in a region displayed on a mobile device in order to focus the mobile device's camera prior to taking an image of the test results of the lateral flow assay device, according to various aspects of the present disclosure. The figure as shown, includes three stages 501-503.

With reference to FIG. 5, stage 501 shows that the camera of the mobile device 400 is pointed towards the lateral flow assay device 100. However, only the image 572 of the marker 172 is fitted inside the region 440. As shown in stage 501, the UI 405 may continue displaying the message 430.

In stage 502, the position of the mobile device 400 with respect to the lateral flow assay device 400 is changed and the images 571-572 of two of the markers 171-172 are fitted in the region 440. In stage 502, the UI 405 may continue displaying the message 430.

As shown in stage 503, the position of the mobile device 400 with respect to the lateral flow assay device 400 is further changed such that the images 571-574 of all markers 0171-174 are fit inside the region 440. The LFA test results reader application 414 may remove the message 430 from the UI 405 and may generate a signal to alert the user not to further change the position of the mobile device 400. The signal may be, for example, and without limitation, vibrating (as shown by 590) the mobile device, sounding an audible alert, displaying a message on the UI 405, etc.

Once the images 571-574 of the markers 0171-174 are within the region 440, the LFA test results reader application 414 may use the known distance of the control line 130 of the lateral flow assay device to the markers 0171-174 to identify the location of the image 530 of the control line 130 on the display 410 of the mobile device 130 and command the camera of the mobile device 400 to focus on the control line 130.

As described above, the control line 130 turns on whether or not the target analyte has been present in the sample that has been applied to the lateral flow assay device. The control line 130 is, therefore, a non-white area on which the camera of the mobile device 400 can focus upon completion of the lateral flow assay device's test. Furthermore, the control line 130 and the test line(s) 120 (FIGS. 1A-1B) are on the same plane (which is different than the surface 180 of the housing 100). Locating the control line 130 and focusing on the control line 130 may, therefore, provide the technical advantage of generating sharper images of the test results of the lateral flow assay device. Alternatively, some embodiments may place a colored line on the membrane of the lateral flow assay device, such that the colored line may be visible through the viewing window 110. These embodiments may determine that the binding time period specified by the test manufacturer has passed and may focus the camera of the mobile device on the colored line, as opposed to focusing on the control line 130.

It should be noted that some embodiments may not include the markers 171-174. Some of these embodiments may use one or more point (e.g., one or more corners) of the color bar 155, one or more points (e.g., one or more corners) of the grayscale strip 145, and/or one or more points (e.g., one or more corners) of the viewing window 110 as markers. In these embodiments, the message 430 may instruct the user to position the images of the color bar 155, the grayscale strip 145, and/or the viewing window 110 within the region 440.

Some embodiments that do not include the markers 171-174 may process one or more images taken in stages 501-503 of FIG. 5 and find the location of the color bar, the grayscale strip, and/or the control line by finding the patterns that correspond to the color bar, the grayscale strip, and/or the control line, respectively. The images may be processed, for example, and without limitations, by searching the images for groups of pixels with color values that closely match the known color values of pixels of the color bar's color lines, by searching the images for groups of pixels with intensity values that closely match the known intensity values of pixels of the grayscale strip's intensity lines, and/or by searching the images for groups of pixels that both closely match the known color values of control line after the control line is turned on and also form a narrow line with contrast to its background (normally close to a white background).

Figure 6A:
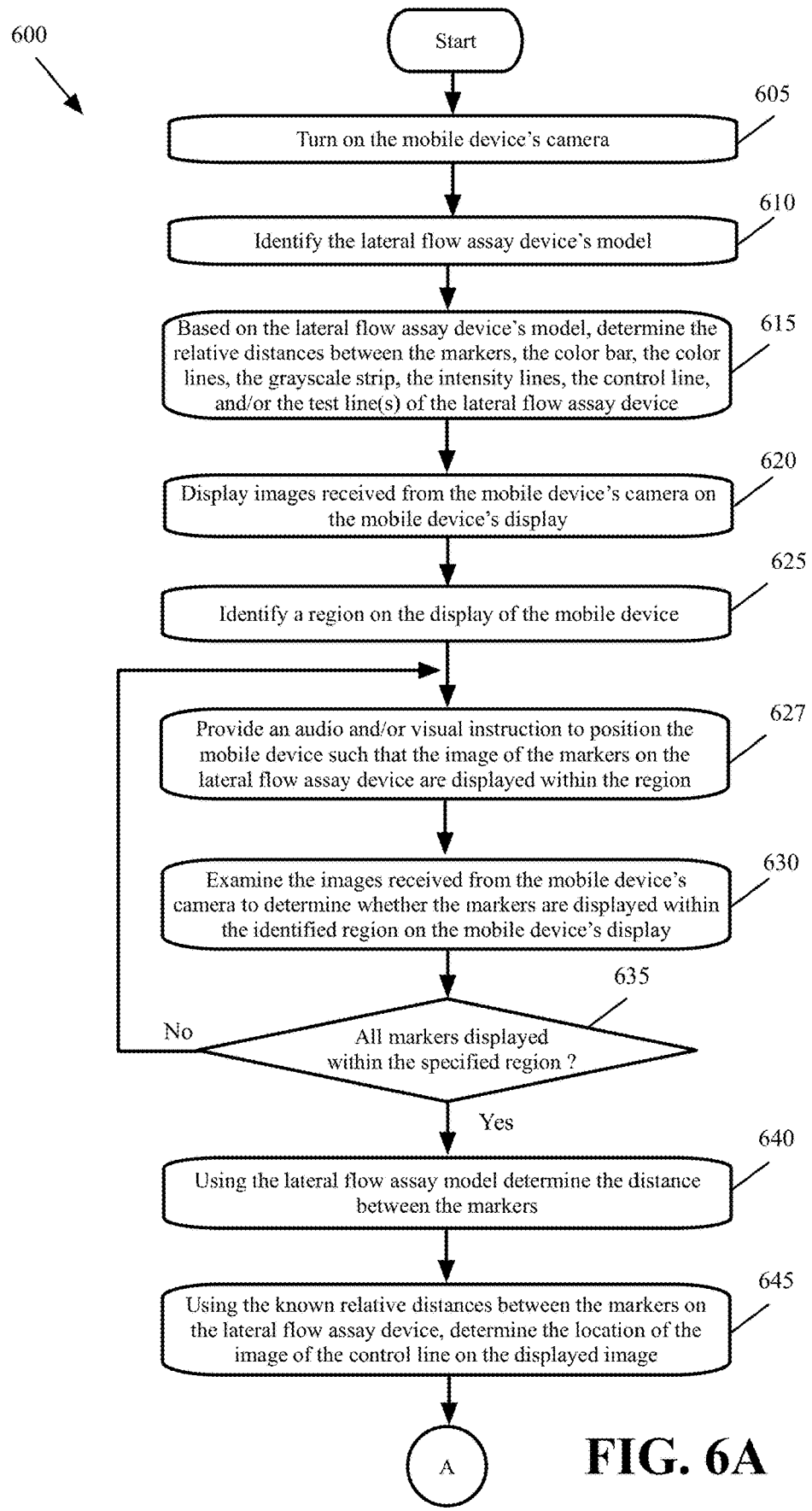
FIGS. 6A-6B show a flowchart illustrating an example process for focusing a mobile device's camera on the control line of a lateral flow assay device, taking an image of the test result, and correcting different parameters of the image, according to various aspects of the present disclosure.
Figure 6B:
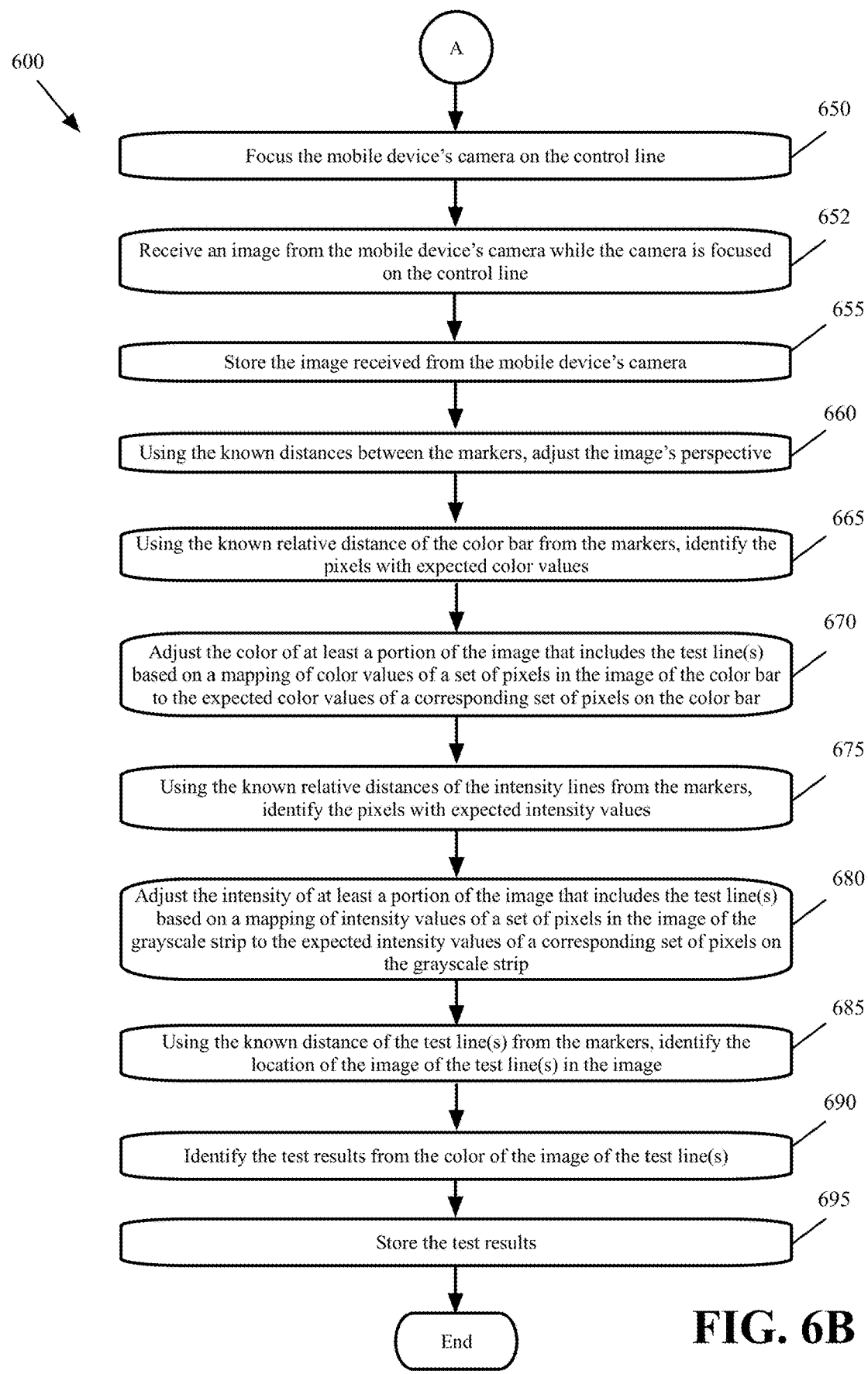

FIGS. 6A-6B show a flowchart illustrating an example process 600 for focusing a mobile device's camera on the control line of a lateral flow assay device, taking an image of the test result, and correcting different parameters of the image, according to various aspects of the present disclosure. In some of the present embodiments, the process 600 may be performed by a processor of a mobile device (e.g., the processor of the mobile device 400 of FIGS. 4-5) that may be used to take images of the test results of a lateral flow assay device.

With reference to FIGS. 6A-6B, the mobile device's camera may be turned on (at block 605). For example, the LFA test results reader application 414 of FIG. 4 may turn on the camera of the mobile device 400 in stage 402 after the activation of the LFA test results reader application 414.

The lateral flow assay device's model may be determined (at block 610). For example, the test results reader application program 414, in some embodiments, may read the lateral flow assay device's model from the barcode 190 (FIG. 1A) from an image of the lateral flow assay device taken by the camera of the mobile device 400.

In some embodiments, the mobile device 400 may be NFC enabled and the test results reader application program 414, in some embodiments, may read the lateral flow assay device's model from the NFC chip. In other embodiments, the model of the lateral flow assay device may be received through the UI 405 of the mobile device 400.

With further reference to FIGS. 6A-6B, based on the lateral flow assay device's model, the relative distances between the markers, the color bar, the color lines, the grayscale strip, the intensity lines, the control line, and/or the test line(s) of the lateral flow assay device may be determined (at block 615). For example, each lateral flow assay model may have a known dimension and a known relative distance between the markers 171-174 and one or more other items on the housing of the lateral flow assay devices, such as, for example, and without limitations, one or more points on the color bar, the color lines, the grayscale strip, the intensity lines, the control line, and/or the test line(s).

The test results reader application program 414 may store the known dimension and the known positions of the markers 171-174 and the control line 130 for each lateral flow assay device model. Once the lateral flow assay's model is known, the test results reader application program 414 may perform, for example, a table lookup to determine the relative distance between the markers 171-174, the color bar 155, the color lines 150, the grayscale strip 145, the intensity lines 140, the control line 130, and/or the test line(s) 120 the lateral flow assay device.

Images received from the mobile device's camera may be displayed (at block 620) on the display of the mobile device. For example, as shown in stage 501-503 of FIG. 5, the images received from the mobile device's camera may be displayed on the display 410 of the mobile device 400.

A region may be identified (at block 625) on the display of the mobile device. For example, the region 440 may be displayed on the display 410 of the mobile device 400, as shown in stage 402 of FIG. 4. An audio and/or visual instruction may be provided (at block 627) to position the mobile device such that the image of the markers on the lateral flow assay device may be displayed within the region.

For example, the message 430 may be displayed on the display 130 of the mobile device, as shown in stage 501 of FIG. 5. In addition to, or in lieu of the message 430, a voice message may be played on the speaker of the mobile device 400 to position the mobile device such that the image of the markers on the lateral flow assay device's housing may be displayed within the region.

The images received from the mobile device's camera may be examined (at block 630) to determine whether the markers are displayed within the identified region on the mobile device's display. For example, the LFA test results reader application 414 may examine the images received from the mobile device's camera to determine whether the images 571-574 of all markers 171-174 are fitted inside the region 440, as described with reference to stages 501-503 of FIG. 5.

Next, a determination may be made (at block 635) whether all markers are displayed within the specified region. If not, the process 600 may proceed to block 627, which was described above. For example, when the images 571-574 of all markers 171-174 are not fitted inside the region 440, the LFA test results reader application 414 may continue displaying the message 430 on the display 410 of the mobile device 400, as described above with reference to stages 501 and 502 of FIG. 5.

When all markers are displayed within the specified region, the distance between the markers may be determined (at block 640). Using the known relative distance between the markers on the lateral flow assay device, the location of the control line on the image may be identified (at block 645).

For example, as described above with reference to stage 503 of FIG. 5, when all markers 171-174 are displayed within the specified region 440, the distance between the markers and the control line may be determined and the location of the image 530 of the control line 530 on the image may be determined (at block 645).

Next, the mobile device's camera may be focused (at block 650) on the control line. Since the control line 130 (FIGS. 1A-1B) and the test line(s) 120 are in the same plane, focusing the camera on the control line 130 may also focus the camera on the test line(s) 120 and may produce sharper images of the control line and the test line(s).

Next, an image may be received (at block 652) from the mobile device's camera while the camera is focused on the control line. For example, while the camera is focused on the control line, the LFA test results reader application 414 may send one or more signals to the mobile device's camera to take a picture. The image received from the mobile device's camera may then be stored (at block 655).

Figure 7:
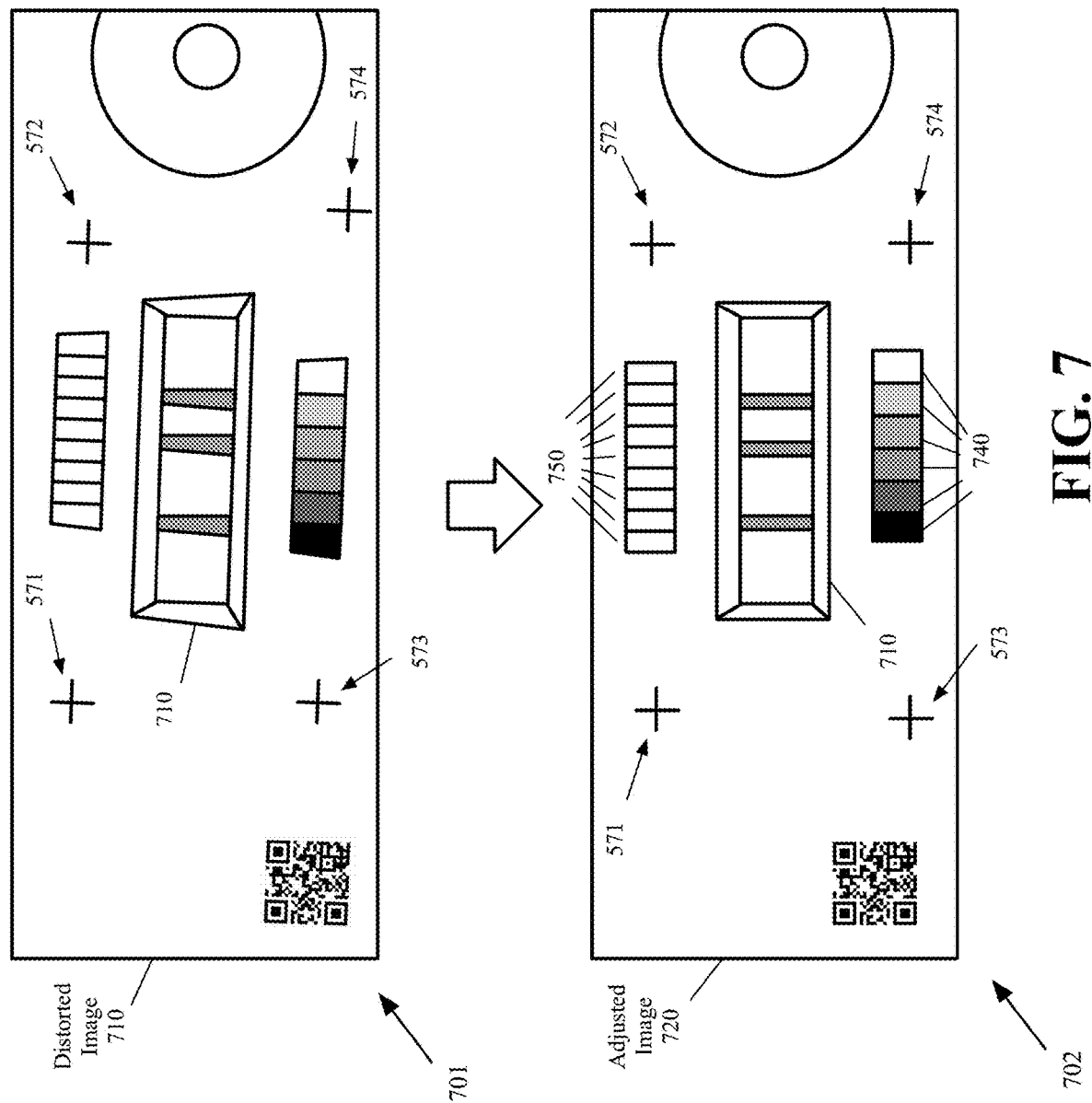
FIG. 7 a is functional diagram showing perspective corrections of an image taken from the test results of a lateral flow assay device, according to various aspects of the present disclosure.

Next, the image's perspective may be adjusted (at block 660) by using the known distances between the markers. FIG. 7 is a functional diagram showing perspective corrections of an image taken from the test results of a lateral flow assay device, according to various aspects of the present disclosure. The figure, as shown, includes two stages 701-702.

With reference to FIG. 7, stage 701 shows an image 710 that is taken by the camera of the mobile device 400 of FIG. 5. Since the mobile device may not have been held at a parallel plane to the top surface 180 (FIG. 1A) of the lateral flow assay device and/or the mobile device may not have been held directly on top of the test viewing window 110, the image 710 may be distorted.

For example, the markers 171-174 (FIGS. 1A-1B) may form the four corners of a rectangle, but the images 571-574 of the four markers 171-174 in stage 701 of FIG. 7 may not form the four corners of a rectangle. As another example, the distance between the images 571 and 572 of the markers 171 and 172 may not be equal to the distance between the images 573 and 574 of the markers 173 and 174. Furthermore, the test viewing window 110 (FIGS. 1A-1B) may be a rectangle but the image 710 of the test viewing window in stage 701 of FIG. 7 may not be a rectangle, etc.

As shown by the adjusted image 720 in stage 702, the perspective of the image may be corrected. For example, the images 571-574 of the four markers 171-174 may form the four corners of a rectangle or the image 510 of the test viewing window may be a rectangle, etc.

Referring back to FIGS. 6A-6B, using the known relative distances of the color bar from the markers, the pixels with expected color values may be identified (at block 665) on the image. For example, as described above with reference to block 615, the relative distances between the markers 171-174 and the color lines 150 may be determined based on the lateral flow assay device's model.

The relative distances between the markers and the color bar may then be used to interpolate and/or extrapolate the distances on the adjusted image 720 (FIG. 7) to identify the location of the image 750 of each color line in the adjusted image 720. With reference to FIGS. 6A-6B, the color of at least a portion of the image that includes the image of the test line(s) may be adjusted (at block 670) based on a mapping of the color values of a set of pixels in the image of the color bar to the expected color values of a corresponding set of pixels on the color bar.

In some embodiments, the mapping, at block 670, may include calculating the differences between the expected color values of the pixels on the color bar and the color values of the corresponding pixels in captured on the image. A function of the differences may be then calculated and applied to other pixels of the image. In some embodiments, the color adjustment may be performed for a portion of the image that includes the test line(s) and the control line. In some embodiments, the color of the entire image may be adjusted.

In some embodiments, the mapping, at block 670, may include using machine learning. In these embodiments, the machine learning algorithm may be trained by taking images of a plurality of pixels on the color bar, which may be used during training as the know output of the machine learning algorithm. After the machine learning algorithm is trained, the algorithm may be used, at block 670, to adjust the color values of the image.

With continued reference to FIGS. 6A-6B, using the known relative distances of the grayscale strip from the markers, the pixels with expected intensity values may be identified (at block 675). For example, as described above with reference to block 615, the relative distances between the markers 171-174 and the intensity lines 140 may be determined based on the lateral flow assay device's model.

The relative distances may then be used to interpolate and/or extrapolate the distances on the adjusted image 720 to identify the location of the image 740 of each intensity line in the adjusted image 720. The intensity of at least a portion of the image that includes the image of the test line(s) may then be adjusted (at block 680) based on a mapping of the intensity values of a set of pixels in the image of the grayscale strip to expected intensity values of a corresponding set of pixels on the grayscale strip.

In some embodiments, the mapping, at block 680, may include calculating the differences between the expected intensity values of the pixels on the grayscale strip and the intensity values of the corresponding pixels in the captured on the image. A function of the differences may be then calculated and applied to other pixels of the image. In some embodiments, intensity adjustment may be performed for a portion of the image that includes the test line(s) and the control line. In some embodiments, the intensity of the entire image may be adjusted.

In some embodiments, the mapping, at block 680, may include using machine learning. In these embodiments, the machine learning algorithm may be trained by taking images of a plurality of pixels on the grayscale strip, which may be used during training as the know output of the machine learning algorithm. After the machine learning algorithm is trained, the algorithm may be used, at block 680, to adjust the intensity values of the pixels of the image.

In certain color and intensity correction algorithms, the color and intensity information from the color bar and the grayscale strip maybe used collectively to correct the color and intensity of the final image. The color bar may also include a white area. In some of the correction algorithms known as white balancing, this white reference area may be the only reference that is used for the correction.

With further reference to FIGS. 6A-6B, the location of the image of the test line(s) may then be identified (at block 685) in the image by using the known relative distances of the test line(s) from the markers. The test results may then be identified (at block 690) from the color, intensity and contrast of the image of the test line(s). The test results may then be stored (at block 695). The process 600 may then end.

The specific operations of the process 600 may not be performed in the exact order shown and described. Furthermore, the specific operations described with reference to FIGS. 6A-6B may not be performed in one continuous series of operations, in some aspects of the present disclosure, and different specific operations may be performed in different embodiments.

For instance, in some aspects of the present embodiments, the color correction (at block 670) and the intensity adjustment (at block 680) may be performed using one algorithm. In other embodiments, separate color adjustment and intensity adjustment algorithms may be used. Different embodiments may use one or more different algorithms, such as, for example, and without limitations the Gray World Theory (GWT) algorithm, the Retinex Theory/Perfect Reflector algorithm, the Gray World/Retinex Theory algorithm, the Standard Deviation-Weighted Gray World algorithm, the Standard Deviation and Luminance-weighted Gray World algorithm, the Adjacent Channels Adjustment by Standard Deviation and Luminance algorithm, the White Patches in YCbCr Color Space, etc., which are used to do white balancing, color adjustment, and/or intensity adjustments.

As another example, some embodiments may not include a grayscale strip. In these embodiments, blocks 675 and 680 may be skipped. As another example, some embodiments may not include a color bar. In these embodiments, blocks 665 and 670 may be skipped.

As another example, some embodiments may process one or more images of the lateral flow assay device and find the location of the color bar, the grayscale strip, and/or the control line by finding the patterns that correspond to the color bar, the grayscale strip, and/or the control line, respectively. In some of these embodiments, blocks 615, 640, and 645 may be skipped and in block 630 the images may be processed, for example, and without limitations, by searching the images for groups of pixels with color values that closely match the known color values of pixels of the color bar's color lines, by searching the images for groups of pixels with intensity values that closely match the known intensity values of pixels of the grayscale strip's intensity lines, and/or by searching the images for groups of pixels that both closely match the known color values of control line after the control line is turned on and also form a narrow line with contrast to its background (normally close to a white background). Based on the processing of the images, a determination may be made (at block 635) whether the color bar, the grayscale strip, and/or the control lines are within the specified region. The perspective may then be adjusted (at block 660) using the relative distances of the color bar, the grayscale strip, and/or the control. The relative distances of the color bar, the grayscale strip, and/or the control may be used (at block 685) to find the location of test line(s).

Many of the above-described features and applications may be implemented as software processes that are specified as a set of instructions recorded on a computer readable storage medium (also referred to as computer readable medium). When these instructions are executed by one or more processors (e.g., cores of processors, one or more single-core processors, one or more multi-core processors, or other processing units), they cause the processor(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions may be implemented as sub-parts of a larger program while remaining distinct software inventions. In some embodiments, multiple software inventions may also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 8:
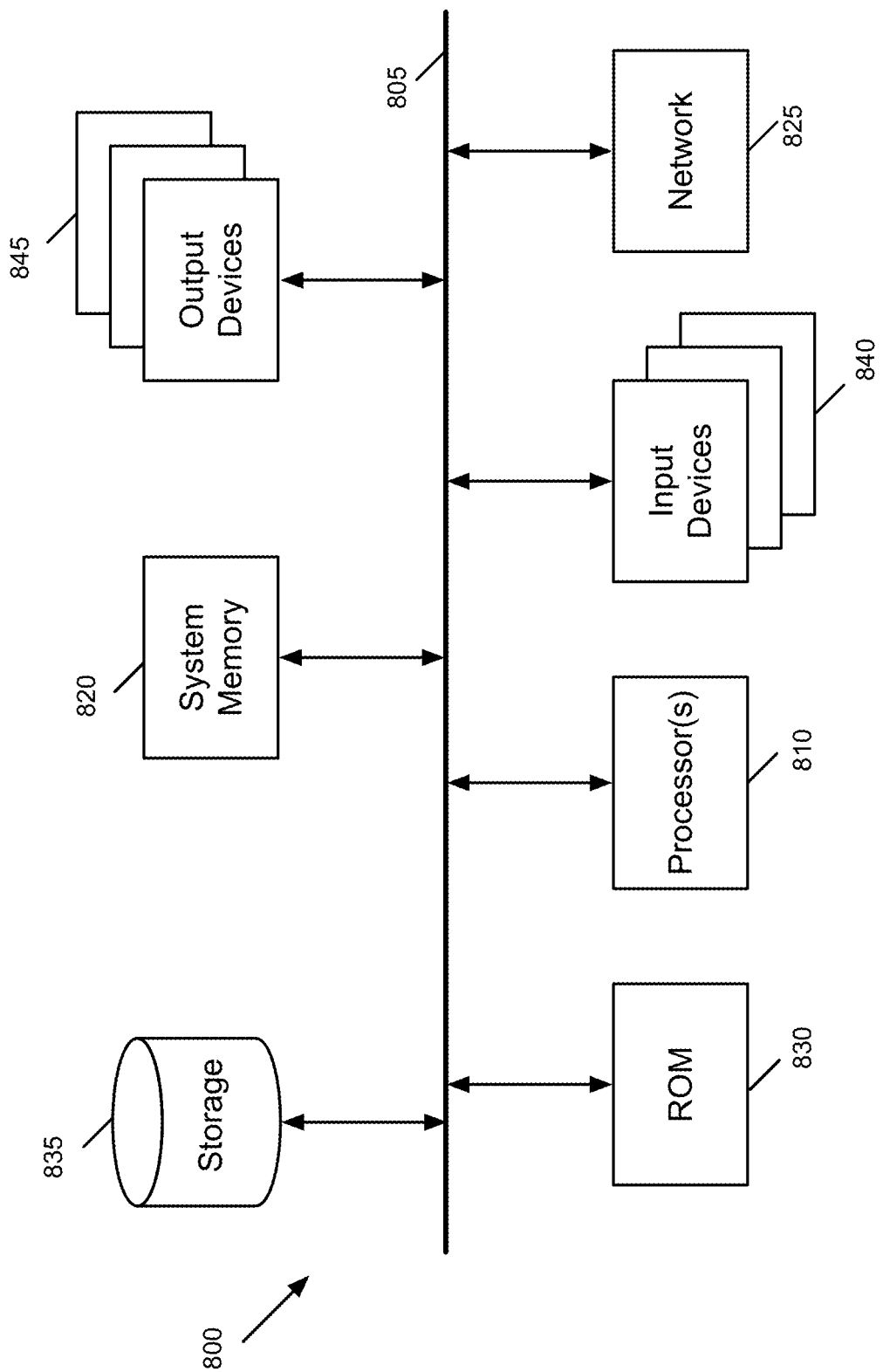
FIG. 8 is a functional block diagram illustrating an example electronic system, according to various aspects of the present disclosure.

FIG. 8 is a functional block diagram illustrating an example electronic system 800, according to various aspects of the present disclosure. With reference to FIG. 8, some embodiments of the invention, such as for example, and without limitations, the mobile device described above, may be implemented using the electronic system 800. The electronic system 800 may be used to execute any of the processes, methods, controls, virtualization, or operating system applications described above. The electronic system 800 may be a computer (e.g., a desktop computer, a personal computer, a tablet computer, a server computer, a mainframe, a blade computer etc.), phone (e.g., a smartphone), personal digital assistant (PDA), or any other sort of electronic device. Such an electronic system may include various types of computer readable media and interfaces for various other types of computer readable media. The electronic system 800 may include a bus 805, processor(s) 810, a system memory 820, a read-only memory (ROM) 830, a permanent storage device 835, input devices 840, and output devices 845.

The bus 805 may collectively represent all system, peripheral, and chipset buses that communicatively connect the numerous internal devices of the electronic system 800. For example, the bus 805 may communicatively connect the processor(s) 810 with the read-only memory 830, the system memory 820, and the permanent storage device 835. From these various memory units, the processor(s) 810 may retrieve instructions to execute and data to process in order to execute the processes of the invention.

The read-only-memory 830 may store static data and instructions that are needed by the processor(s) 810 and other modules of the electronic system. The permanent storage device 835, on the other hand, may be a read-and-write memory device. This device is a non-volatile memory unit that may store instructions and data even when the electronic system 800 is off. Some embodiments of the invention may use a mass-storage device (such as a magnetic or optical disk and its corresponding disk drive) as the permanent storage device 835.

Other embodiments may use a removable storage device (such as a flash drive, etc.) as the permanent storage device. Like the permanent storage device 835, the system memory 820 may be a read-and-write memory device. However, unlike storage device 835, the system memory may be a volatile read-and-write memory, such as random access memory. The system memory may store some of the instructions and data that the processor needs at runtime. In some embodiments, the invention's processes may be stored in the system memory 820, the permanent storage device 835, and/or the read-only memory 830. From these various memory units, the processor(s) 810 may retrieve instructions to execute and data to process in order to execute the processes of some embodiments.

The bus 805 may also connect to the input and output devices 840 and 845. The input devices may enable the user to communicate information and select commands to the electronic system. The input devices 840 may include one or more cameras, alphanumeric keyboards, pointing devices (also called "cursor control devices"). The output devices 845 may display images generated by the electronic system. The output devices may include printers and display devices, such as cathode ray tubes (CRT) or liquid crystal displays (LCD). Some embodiments may include devices such as a touchscreen that function as both input and output devices.

Finally, as shown in FIG. 8, the bus 805 may also couple the electronic system 800 to a network 825 through one or more wireless transceivers and/or a network adapter (not shown). In this manner, the computer may be a part of a network of computers (such as a local area network ("LAN"), a wide area network ("WAN"), an Intranet, or a network of networks, such as the Internet. Any or all components of the electronic system 800 may be used in conjunction with the invention.

Some embodiments may include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, and any other optical or magnetic media. The computer-readable media may store a computer program that is executable by at least one processor and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some embodiments may be performed by one or more integrated circuits, such as application specific integrated circuits (ASICs) or field programmable gate arrays (FPGAs). In some embodiments, such integrated circuits may execute instructions that are stored on the circuit itself.

As used in this specification, the terms "computer", "server", "processor", and "memory" all refer to electronic or other technological devices. These terms exclude people or groups of people. For the purposes of the specification, the terms display or displaying means displaying on an electronic device. As used in this specification, the terms "computer readable medium," "computer readable media," and "machine readable medium" are entirely restricted to tangible, physical objects that store information in a form that is readable by a computer. These terms exclude any wireless signals, wired download signals, and any other ephemeral or transitory signals.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. An automated method of determining a test result of a lateral flow assay device, the method comprising:
    displaying images received from a camera of a mobile device on a display of the mobile device;
    by a processor of the mobile device, determining that images of a plurality of markers on a housing of the lateral flow assay device are displayed within a region on the display of the mobile device;
    by the processor of the mobile device, identifying a location of an image of a control line of the lateral flow assay device based on relative distances from the markers to one or more pixels on the image of the control line, the control line located on a membrane of the lateral flow assay device;

focusing the camera of the mobile device on the control line of the lateral flow assay device;

by the processor of the mobile device, receiving a captured image from the focused camera, the captured image comprising an image of the control line, an image of a set of one or more test lines located on the membrane, and an image of a color bar on the housing of the lateral flow assay device;

by the processor of the mobile device, adjusting colors of pixels of at least a portion of the captured image that comprises the image of the set of test lines based on a mapping of color values of a set of pixels in the image of the color bar to the expected color values of a corresponding set of pixels on the color bar; and after adjusting the colors of the pixels of the portion of the captured image, identifying, by the processor of the mobile device, the test result of the lateral flow assay device from colors of a plurality of pixels of the image of the set of test lines.

2. The automated method of claim 1 further comprising adjusting a perspective of the captured image by the processor of the mobile device based on known relative distances between a plurality of pairs of the markers on the housing of the lateral flow assay device and distances of the images of the corresponding pairs of the markers in the captured image.

3. The automated method of claim 1 further comprising:
by the processor of the mobile device, identifying the lateral flow assay device's model; and
determining the relative distances from the markers to the one or more pixels on the image of the control line by making a table lookup based on the lateral flow assay device's model.

4. The automated method of claim 3, wherein identifying the lateral flow assay device's model comprises one of (i) receiving the model from a near field communication (NFC) chip of the lateral flow assay device, (ii) reading the model from an image of a barcode of the lateral flow assay device taken by the camera of the mobile device, and (iii) receiving the model from a user interface of the mobile device.

5. The automated method of claim 1 further comprising:
prior to adjusting the colors of pixels of the portion of the captured image, identifying a location of the set of pixels on the color bar by the processor of the mobile device based on known relative distances of the set of pixels on the color bar to one or more of the markers.

6. The automated method of claim 1, wherein the captured image comprises an image of a grayscale strip, the method further comprising:
prior to identifying the test result, adjusting intensities of pixels of a portion of the captured image by the processor of the mobile device based on a mapping of intensity values of a set of pixels in the image of the grayscale strip to expected intensity values of a corresponding set of pixels on the grayscale strip,
wherein identifying the test result of the lateral flow assay device further comprises identifying the test result from intensity of a plurality of pixels of the image of the set of test lines.

7. The automated method of claim 6 further comprising:
prior to adjusting the intensities of the pixels of the portion of the captured image, identifying a location of the set of pixels on the grayscale strip based on known distances of the set of pixels on the grayscale strip to one or more of the markers.

8. The automated method of claim 1 further comprising:
by the processor of the mobile device, providing one or more audio or visual instructions to position the mobile device such that the image of the plurality of makers on the lateral flow assay device are displayed within the region on the display of the mobile device.

9. An automated method of determining a test result of a lateral flow assay device, the method comprising:
displaying images received from a camera of a mobile device on a display of the mobile device;
by a processor of the mobile device, determining that images of a plurality of markers on a housing of the lateral flow assay device are displayed within a region on the display of the mobile device;
by the processor of the mobile device, identifying a location of an image of a control line of the lateral flow assay device based on relative distances from the markers to one or more pixels on the image of the control line, the control line located on a membrane of the lateral flow assay device;
focusing the camera of the mobile device on the control line of the lateral flow assay device;
by the processor of the mobile device, receiving a captured image from the focused camera, the captured image comprising an image of the control line, an image of a set of one or more test lines located on the membrane, an image of a color bar on the housing of the lateral flow assay device, and an image of a grayscale strip on the housing of the lateral flow assay device;
by the processor of the mobile device, adjusting colors and intensities of pixels of at least a portion of the captured image that comprises the image of the set of test lines based on expected color values of a set of pixels on the color bar, expected intensity values of a set of pixels on the grayscale strip, color values of a set of pixels in the image of the color bar, and intensity values of a set of pixels in the image of the grayscale strip; and
after adjusting the colors and intensities of the pixels of the portion of the captured image, identifying, by the processor of the mobile device, the test result of the lateral flow assay device from colors and intensities of a plurality of pixels of the image of the set of test lines.

10. The automated method of claim 9 further comprising adjusting a perspective of the captured image by the processor of the mobile device based on known distances between a plurality of pairs of the markers on the housing of the lateral flow assay device and distances of the images of the corresponding pairs of the markers in the captured image.

11. The automated method of claim 9 further comprising:
by the processor of the mobile device, identifying the lateral flow assay device's model; and
determining the relative distances from the markers to the one or more pixels on the image of the control line by making a table lookup based on the model of the lateral flow assay device's model.

12. The automated method of claim 11, wherein identifying the lateral flow assay device's model comprises one of (i) receiving the model from a near field communication (NFC) chip of the lateral flow assay device, (ii) reading the model from an image of a barcode of the lateral flow assay device taken by the camera of the mobile device, and (iii) receiving the model from a user interface of the mobile device.

13. The automated method of claim 9 further comprising:
prior to adjusting the colors and the intensities of the pixels of the portion of the captured image:
identifying, by the processor of the mobile device, a location of the set of pixels on the color bar based on known relative distances of the set of pixels on the color bar to one or more of the markers; and
identifying, by the processor of the mobile device, a location of the set of pixels on the grayscale strip based on known relative distances of the set of pixels on the grayscale strip to one or more of the markers.

14. A non-transitory computer readable medium storing a program for determining a test result of a lateral flow assay device, the program executable by a processor of a mobile device, the program comprising sets of instructions for:
displaying images received from a camera of the mobile device on a display of the mobile device;
determining that images of a plurality of markers on a housing of the lateral flow assay device are displayed within a region on the display of the mobile device;
identifying a location of an image of a control line of the lateral flow assay device based on relative distances from the markers to one or more pixels on the image of the control line, the control line located on a membrane of the lateral flow assay device;
focusing the camera of the mobile device on the control line of the lateral flow assay device;
receiving a captured image from the focused camera, the captured image comprising an image of the control line, an image of a set of one or more test lines located on the membrane, and an image of a color bar on the housing of the lateral flow assay device;
adjusting colors of pixels of at least a portion of the captured image that comprises the image of the set of test lines based on a mapping of color values of a set of pixels in the image of the color bar to the expected color values of a corresponding set of pixels on the color bar; and
after adjusting the colors of the pixels of the portion of the captured image, identifying, the test result of the lateral flow assay device from colors of a plurality of pixels of the image of the set of test lines.

15. The non-transitory computer readable medium of claim 14 further comprising a set of instructions for adjusting a perspective of the captured image based on known relative distances between a plurality of pairs of the markers on the housing of the lateral flow assay device and distances of the images of the corresponding pairs of the markers in the captured image.

16. The non-transitory computer readable medium of claim 14 further comprising:
a set of instructions for identifying the lateral flow assay device's model; and
a set of instructions for determining the relative distances from the markers to the one or more pixels on the image of the control line by making a table lookup based on the lateral flow assay device's model.

17. The non-transitory computer readable medium of claim 16, wherein the set of instructions for identifying the lateral flow assay device's model comprises one of (i) a set of instructions for receiving the model from a near field communication (NFC) chip of the lateral flow assay device, (ii) a set of instructions for reading the model from an image of a barcode of the lateral flow assay device taken by the camera of the mobile device, and (iii) a set of instructions for receiving the model from a user interface of the mobile device.

18. The non-transitory computer readable medium of claim 14 further comprising a set of instructions for identifying a location of the set of pixels on the color bar based on known relative distances of the set of pixels on the color bar to one or more of the markers prior to adjusting the colors of pixels of the portion of the captured image.

19. The non-transitory computer readable medium of claim 14 further comprising sets of instructions for:
identifying an image of a grayscale strip in the captured image;
identifying a location of the set of pixels on the grayscale strip based on known distances of the set of pixels on the grayscale strip to one or more of the markers prior to adjusting the intensities of the pixels of the portion of the captured image; and
adjusting, prior to identifying the test result, intensities of pixels of a portion of the captured image based on a mapping of intensity values of a set of pixels in the image of the grayscale strip to expected intensity values of a corresponding set of pixels on the grayscale strip,
wherein the set of instructions for identifying the test result of the lateral flow assay device further comprises a set of instructions for identifying the test result from intensity of a plurality of pixels of the image of the set of test lines.

20. The non-transitory computer readable medium of claim 14 further comprising a set of instructions for providing one or more audio or visual instructions to position the mobile device such that the image of the plurality of makers on the lateral flow assay device are displayed within the region on the display of the mobile device.

* * * * *